(12) United States Patent
Sowards et al.

(10) Patent No.: US 12,089,815 B2
(45) Date of Patent: Sep. 17, 2024

(54) FIBER OPTIC MEDICAL SYSTEMS AND DEVICES WITH ATRAUMATIC TIP

(71) Applicant: Bard Access Systems, Inc., Salt Lake City, UT (US)

(72) Inventors: Steffan Sowards, Salt Lake City, UT (US); William Robert Mclaughlin, Bountiful, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/697,895

(22) Filed: Mar. 17, 2022

(65) Prior Publication Data

US 2023/0292997 A1    Sep. 21, 2023

(51) Int. Cl.
*A61B 1/00* (2006.01)
*A61B 1/07* (2006.01)

(52) U.S. Cl.
CPC ...... *A61B 1/00167* (2013.01); *A61B 1/00043* (2013.01); *A61B 1/00096* (2013.01); *A61B 1/00098* (2013.01); *A61B 1/07* (2013.01)

(58) Field of Classification Search
CPC ............. A61B 1/0008; A61B 1/00096; A61B 1/00117; A61B 1/00126; A61B 1/00165; A61B 1/00167; A61B 1/0017; A61B 1/0051; A61B 1/0058; A61B 1/07; A61B 1/00098; A61B 1/00043
USPC ................................................. 600/182, 129
See application file for complete search history.

(56) References Cited

U.S. PATENT DOCUMENTS

| | | |
|---|---|---|
| 3,493,288 A | 2/1970 | Oltman et al. |
| 4,813,429 A | 3/1989 | Eshel et al. |
| 5,099,845 A | 3/1992 | Besz et al. |
| 5,163,935 A | 11/1992 | Black et al. |
| 5,178,153 A | 1/1993 | Einzig |
| 5,207,672 A | 5/1993 | Roth et al. |

(Continued)

FOREIGN PATENT DOCUMENTS

| | | |
|---|---|---|
| CA | 3025240 A1 | 11/2017 |
| DE | 102016109601 A1 | 11/2017 |

(Continued)

OTHER PUBLICATIONS

PCT/US2022/043698 filed Sep. 15, 2022 International Search Report and Written Opinion dated Dec. 19, 2022.

(Continued)

*Primary Examiner* — Timothy J Neal
*Assistant Examiner* — James Edward Boice
(74) *Attorney, Agent, or Firm* — Rutan & Tucker LLP

(57) ABSTRACT

Disclosed herein are medical systems and devices that include an elongate probe configured for insertion into a patient, where the elongate probe includes an atraumatic tip and where the atraumatic tip includes one or more of a loop, a curl, coil, a flexible distal tip section, a steerable distal tip section, a distal tip section configured to transition away from a first shape toward a second shape upon insertion of the elongate probe within the patient. The optical fiber includes sensing core fibers configured to facilitate a determination of a physical state of the elongate probe. The elongate probe is also configured to project illuminating light away from a distal end and receive imaging light at the distal end.

17 Claims, 8 Drawing Sheets

(56) References Cited

U.S. PATENT DOCUMENTS

| | | |
|---|---|---|
| 5,211,165 A | 5/1993 | Dumoulin et al. |
| 5,220,703 A | 6/1993 | Kanayama et al. |
| 5,275,151 A | 1/1994 | Shockey et al. |
| 5,423,321 A | 6/1995 | Fontenot |
| 5,454,807 A | 10/1995 | Lennox et al. |
| 5,517,997 A | 5/1996 | Fontenot |
| 5,599,492 A * | 2/1997 | Engelson .............. A61M 25/09 |
| | | 264/209.3 |
| 5,622,170 A | 4/1997 | Schulz |
| 5,633,494 A | 5/1997 | Danisch |
| 5,693,043 A | 12/1997 | Kittrell et al. |
| 5,740,808 A | 4/1998 | Panescu et al. |
| 5,827,313 A | 10/1998 | Ream |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,210,362 B1 | 4/2001 | Ponzi |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Zatt et al. |
| 6,593,884 B1 | 7/2003 | Gilboa et al. |
| 6,597,941 B2 | 7/2003 | Fontenot et al. |
| 6,619,857 B2 | 9/2003 | Miyake |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 6,975,803 B2 | 12/2005 | Koide et al. |
| 7,132,645 B2 | 11/2006 | Kom |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 * | 5/2009 | Ainsworth ......... A61B 5/02007 |
| | | 600/478 |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,197,494 B2 | 6/2012 | Jaggi et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,119,551 B2 | 9/2015 | Qi et al. |
| 9,186,046 B2 | 11/2015 | Ramamurthy et al. |
| 9,339,206 B2 | 5/2016 | Grunwald |
| 9,345,510 B2 | 5/2016 | Patel et al. |
| 9,360,630 B2 | 6/2016 | Jenner et al. |
| 9,560,954 B2 | 2/2017 | Jacobs et al. |
| 9,572,492 B2 | 2/2017 | Simpson et al. |
| 9,622,706 B2 | 4/2017 | Dick et al. |
| 9,645,326 B1 | 5/2017 | Sausse et al. |
| 9,649,048 B2 | 5/2017 | Cox et al. |
| 9,678,275 B1 | 6/2017 | Griffin |
| 9,678,284 B2 | 6/2017 | Coggi et al. |
| 10,231,643 B2 | 3/2019 | Grunwald |
| 10,231,753 B2 | 3/2019 | Burnside et al. |
| 10,258,240 B1 | 4/2019 | Eberle et al. |
| 10,327,830 B2 | 6/2019 | Grant et al. |
| 10,349,890 B2 | 7/2019 | Misener et al. |
| 10,448,837 B2 | 10/2019 | Manzke et al. |
| 10,492,876 B2 | 12/2019 | Anastassiou et al. |
| 10,568,586 B2 | 2/2020 | Begin et al. |
| 10,620,386 B2 | 4/2020 | Van Der Mark et al. |
| 10,631,718 B2 | 4/2020 | Petroff et al. |
| 10,932,670 B2 | 3/2021 | Smith et al. |
| 10,939,889 B2 | 3/2021 | Flexman et al. |
| 10,992,078 B2 | 4/2021 | Thompson et al. |
| 10,992,079 B2 | 4/2021 | Stats et al. |
| 11,000,207 B2 | 5/2021 | Burnside et al. |
| 11,000,265 B1 | 5/2021 | Ryu et al. |
| 11,123,047 B2 | 9/2021 | Jaffer et al. |
| 11,284,916 B2 | 3/2022 | Patel et al. |
| 11,382,653 B2 | 7/2022 | Patel et al. |
| 11,525,670 B2 | 12/2022 | Messerly et al. |
| 11,850,073 B2 | 12/2023 | Wright et al. |
| 2002/0019627 A1 | 2/2002 | Maguire et al. |
| 2002/0166190 A1 | 11/2002 | Miyake et al. |
| 2002/0198457 A1 | 12/2002 | Tearney et al. |
| 2003/0092995 A1 | 5/2003 | Thompson |
| 2004/0111020 A1 | 6/2004 | Long |
| 2004/0111147 A1 | 6/2004 | Rabkin et al. |
| 2004/0242995 A1 | 12/2004 | Maschke |
| 2004/0260182 A1 * | 12/2004 | Zuluaga ............... A61B 5/6885 |
| | | 600/473 |
| 2005/0033264 A1 | 2/2005 | Redinger |
| 2006/0013523 A1 | 1/2006 | Childers et al. |
| 2006/0036164 A1 | 2/2006 | Wilson et al. |
| 2006/0100610 A1 | 5/2006 | Wallace et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0060847 A1 | 3/2007 | Leo et al. |
| 2007/0156019 A1 | 7/2007 | Larkin et al. |
| 2007/0179485 A1 | 8/2007 | Yeik et al. |
| 2007/0201793 A1 | 8/2007 | Askins et al. |
| 2007/0287886 A1 * | 12/2007 | Saadat ............... A61B 1/00097 |
| | | 600/115 |
| 2007/0299425 A1 | 12/2007 | Waner et al. |
| 2008/0034519 A1 | 2/2008 | Fujiwara |
| 2008/0172119 A1 | 7/2008 | Yamasaki et al. |
| 2008/0183128 A1 | 7/2008 | Morriss et al. |
| 2008/0281293 A1 | 11/2008 | Peh et al. |
| 2008/0285909 A1 | 11/2008 | Younge et al. |
| 2009/0005675 A1 | 1/2009 | Grunwald et al. |
| 2009/0018393 A1 * | 1/2009 | Dick .................... A61B 5/0066 |
| | | 600/109 |
| 2009/0062634 A1 | 3/2009 | Say et al. |
| 2009/0137952 A1 | 5/2009 | Ramamurthy et al. |
| 2009/0208143 A1 | 8/2009 | Yoon et al. |
| 2009/0227992 A1 | 9/2009 | Nir et al. |
| 2009/0234328 A1 | 9/2009 | Cox et al. |
| 2009/0253967 A1 | 10/2009 | Gill et al. |
| 2009/0304582 A1 | 12/2009 | Rousso et al. |
| 2009/0318757 A1 | 12/2009 | Singh |
| 2010/0016729 A1 | 1/2010 | Futrell |
| 2010/0030063 A1 | 2/2010 | Lee et al. |
| 2010/0114115 A1 | 5/2010 | Schlesinger et al. |
| 2010/0114190 A1 | 5/2010 | Bendett et al. |
| 2010/0286531 A1 | 11/2010 | Ryan et al. |
| 2010/0292758 A1 | 11/2010 | Lee et al. |
| 2011/0098533 A1 | 4/2011 | Onoda et al. |

(56) References Cited

U.S. PATENT DOCUMENTS

| | | |
|---|---|---|
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0196248 A1 | 8/2011 | Grunwald |
| 2011/0245662 A1 | 10/2011 | Eggers et al. |
| 2011/0295108 A1 | 12/2011 | Cox et al. |
| 2012/0046562 A1 | 2/2012 | Powers et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0096482 A1 | 4/2013 | Bertrand et al. |
| 2013/0104884 A1 | 5/2013 | Vazales et al. |
| 2013/0150732 A1* | 6/2013 | Manzke ............ A61B 1/00045 600/478 |
| 2013/0188855 A1 | 7/2013 | Desjardins et al. |
| 2013/0190741 A1 | 7/2013 | Moll et al. |
| 2013/0204124 A1 | 8/2013 | Duindam et al. |
| 2013/0211246 A1 | 8/2013 | Parasher |
| 2013/0296652 A1 | 11/2013 | Farr |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0058368 A1 | 2/2014 | Hogue |
| 2014/0088413 A1 | 3/2014 | Von Bucsh et al. |
| 2014/0121468 A1 | 5/2014 | Eichenholz |
| 2014/0221829 A1 | 8/2014 | Maitland et al. |
| 2014/0259477 A1 | 9/2014 | Huang |
| 2014/0275997 A1 | 9/2014 | Chopra et al. |
| 2014/0318825 A1 | 10/2014 | Erb et al. |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0301288 A1 | 10/2015 | Thornton, Jr. |
| 2015/0320977 A1 | 11/2015 | Vitullo et al. |
| 2016/0018602 A1 | 1/2016 | Govari et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1* | 11/2016 | Hera ................... A61B 1/307 |
| 2016/0354038 A1 | 12/2016 | Demirtas et al. |
| 2016/0357007 A1 | 12/2016 | Swanson |
| 2017/0017048 A1 | 1/2017 | Coggi et al. |
| 2017/0020394 A1 | 1/2017 | Harrington |
| 2017/0052091 A1 | 2/2017 | Mori |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0303824 A1* | 10/2017 | Schlesinger ....... A61B 1/00096 |
| 2018/0067268 A1 | 3/2018 | Murakami et al. |
| 2018/0095231 A1 | 4/2018 | Lowell et al. |
| 2018/0113038 A1 | 4/2018 | Janabi-Sharifi et al. |
| 2018/0140170 A1 | 5/2018 | Van Putten et al. |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1* | 10/2018 | Landey ............... A61B 1/0058 |
| 2018/0289390 A1 | 10/2018 | Amorizzo et al. |
| 2018/0289927 A1* | 10/2018 | Messerly ............. G01L 1/242 |
| 2018/0339134 A1 | 11/2018 | Leo |
| 2018/0360545 A1 | 12/2018 | Cole et al. |
| 2018/0369432 A1 | 12/2018 | Zaborsky |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0212761 A1 | 7/2019 | Swanson et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374196 A1* | 12/2019 | Courtney ............... A61B 8/445 |
| 2020/0046434 A1 | 2/2020 | Graetzel et al. |
| 2020/0155073 A1 | 5/2020 | Hwang et al. |
| 2020/0188036 A1 | 6/2020 | Ding et al. |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1 | 2/2021 | Thompson et al. |
| 2021/0298680 A1 | 3/2021 | Sowards et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1 | 9/2021 | Tegg et al. |
| 2021/0325172 A1 | 10/2021 | Hendriks et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0034733 A1 | 2/2022 | Misener et al. |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2023/0082991 A1 | 3/2023 | Sowards et al. |
| 2023/0285085 A1 | 9/2023 | Misener et al. |
| 2023/0293243 A1 | 9/2023 | Misener et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0346482 A1 | 11/2023 | Sowards et al. |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |

FOREIGN PATENT DOCUMENTS

| | | | |
|---|---|---|---|
| EP | 2385802 B1 | 8/2013 | |
| EP | 3266383 A1 | 1/2018 | |
| EP | 3545849 A1 | 10/2019 | |
| EP | 3725252 A1 | 10/2020 | |
| WO | 99/64099 A1 | 12/1999 | |
| WO | 1999064099 A1 | 12/1999 | |
| WO | WO-2006080076 A1 * | 8/2006 | ......... A61B 1/00085 |
| WO | 2006122001 A2 | 11/2006 | |
| WO | 2009/155325 A2 | 12/2009 | |
| WO | 2011141830 A1 | 11/2011 | |
| WO | 2011150376 A1 | 12/2011 | |
| WO | 2012064769 A2 | 5/2012 | |
| WO | 2012135339 A1 | 10/2012 | |
| WO | 2014049555 A1 | 4/2014 | |
| WO | 2015055413 A1 | 4/2015 | |
| WO | 2015074045 A2 | 5/2015 | |
| WO | 2016/061431 A1 | 4/2016 | |
| WO | 2016193051 A1 | 12/2016 | |

(56) References Cited

FOREIGN PATENT DOCUMENTS

| | | | |
|---|---|---|---|
| WO | 2018071490 | A1 | 4/2018 |
| WO | 2018/096491 | A1 | 5/2018 |
| WO | 2019037071 | A1 | 2/2019 |
| WO | 2019/046769 | A1 | 3/2019 |
| WO | 2019230713 | A1 | 12/2019 |
| WO | 2020/142470 | A1 | 7/2020 |
| WO | 2021021408 | A1 | 2/2021 |
| WO | 2021030092 | A1 | 2/2021 |
| WO | 2021108688 | A1 | 6/2021 |
| WO | 2021108697 | A1 | 6/2021 |
| WO | 2021144317 | A1 | 7/2021 |
| WO | 2021178578 | A1 | 9/2021 |
| WO | 2022/031613 | A1 | 2/2022 |
| WO | 2022/081586 | A1 | 4/2022 |
| WO | 2022/081723 | A1 | 4/2022 |
| WO | 2022109045 | A1 | 5/2022 |
| WO | 2022115624 | A1 | 6/2022 |
| WO | 2022221608 | A1 | 10/2022 |
| WO | 2023043947 | A1 | 3/2023 |
| WO | 2023172652 | A1 | 9/2023 |
| WO | 2023177822 | A1 | 9/2023 |
| WO | 2023177889 | A1 | 9/2023 |
| WO | 2023200734 | A1 | 10/2023 |
| WO | 2023205257 | A1 | 10/2023 |
| WO | 2023212096 | A1 | 11/2023 |
| WO | 2023212098 | A1 | 11/2023 |
| WO | 2023249952 | A1 | 12/2023 |
| WO | 2024015464 | A1 | 1/2024 |
| WO | 2024123837 | A1 | 6/2024 |

OTHER PUBLICATIONS

U.S. Appl. No. 17/967,794, filed Oct. 17, 2022 Notice of Allowance dated Feb. 15, 2023.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
PCT/US2021 /059755 filed Nov. 17, 2021 International Search Report and Written Opinion dated Apr. 29, 2022.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/060849 filed Nov. 24, 2021 International Search Report and Written Opinion dated Mar. 9, 2022.
U.S. Appl. No. 17/185,777, filed Feb. 25, 2021 Notice of Allowance dated Jun. 10, 2022.
PCT/US2023/014849 filed Mar. 8, 2023 International Search Report and Written Opinion dated Jun. 7, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
U.S. Appl. No. 17/187,536, filed Feb. 26, 2021 Non-Final Office Action dated May 17, 2023.
U.S. Appl. No. 17/217,852, filed Mar. 30, 2021 Non Final Office Action dated Jun. 7, 2023.
U.S. Appl. No. 17/499,644, filed Oct. 12, 2021 Restriction Requirement dated Jul. 11, 2023.
PCT/US2022/024934 filed Apr. 14, 2022 International Search Report and Written Opinion dated Jul. 18, 2022.
PCT/US2023/020042 filed Apr. 26, 2023 International Search Report and Written Opinion dated Sep. 26, 2023.
PCT/US2023/027527 filed Jul. 12, 2023 International Search Report and Written Opinion dated Oct. 16, 2023.
U.S. Appl. No. 17/187,536, filed Feb. 26, 2021 Advisory Action dated Nov. 21, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
PCT/US2023/025757 filed Jun. 20, 2023 International Search Report and Written Opinion dated Sep. 11, 2023.
U.S. Appl. No. 17/187,536, filed Feb. 26, 2021 Final Office Action dated Sep. 20, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/187,536, filed Feb. 26, 2021 Non-Final Office Action dated Dec. 15, 2023.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
U.S. Appl. No. 17/187,536, filed Feb. 26, 2021 Final Office Action dated Jul. 2, 2024.
U.S. Appl. No. 17/696,675, filed Mar. 16, 2022 Non-Final Office Action dated Jun. 11, 2024.
U.S. Appl. No. 17/725,394, filed Apr. 20, 2022 Non-Final Office Action dated Jun. 17, 2024.
U.S. Appl. No. 18/524,620, filed Nov. 30, 2023 Non-Final Office Action dated Jun. 18, 2024.

* cited by examiner

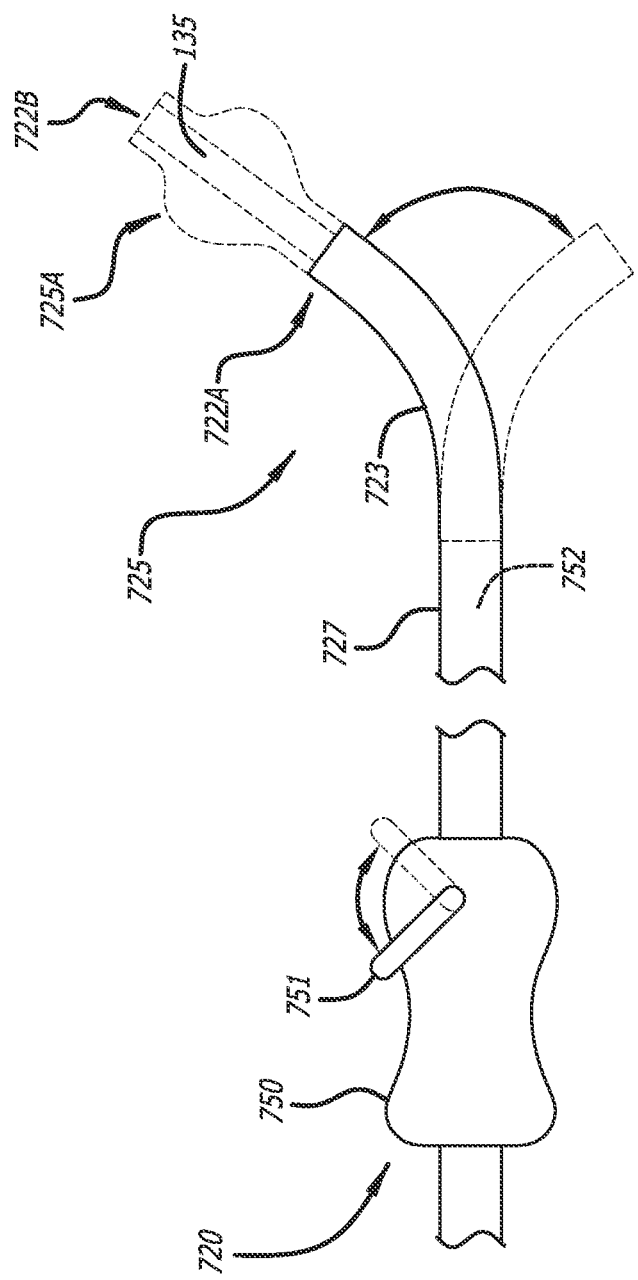
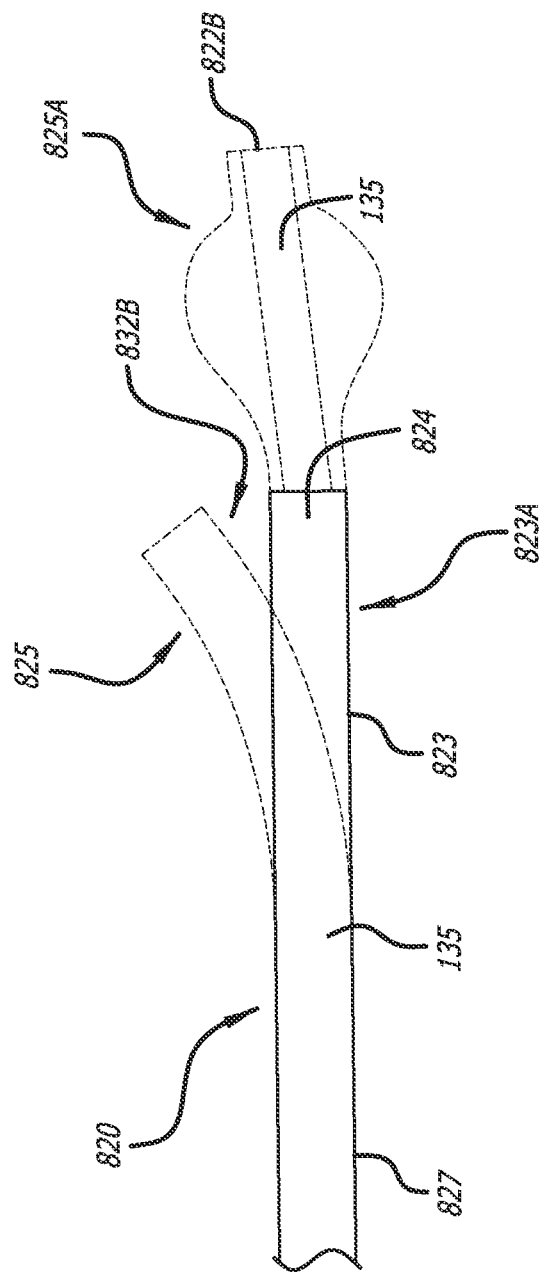

FIBER OPTIC MEDICAL SYSTEMS AND DEVICES WITH ATRAUMATIC TIP

BACKGROUND

The positional monitoring of medical devices during placement within the patient body helps to ensure proper placement in accordance with a defined therapy. In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

Electromagnetic tracking systems have also been utilized to track medical devices, such as devices involving stylets. Electromagnetic tracking systems eliminate radiation exposure associated with fluoroscopic methods and do not require line of site. However, electromagnetic tracking systems generally require multiple component to generate a magnetic field, sense the magnetic field, and interpret magnetic signals. Furthermore, electromagnetic tracking systems are subject to electromagnetic field interference caused by other electronic devices close by. Still further, electromagnetic tracking systems are subject to signal drop out, depend on an external sensor, and are defined to a limited depth range.

In some instances, elongate medical device cause trauma or injury to a patient during insertion into the patient body or advancement along a lumen with the patient body.

As such there is a need for a system to assess the position of medical devices within the patient body that overcomes the negative aspects described above.

SUMMARY

Briefly summarized, disclosed herein is a medical system, according to some embodiments. The system generally includes a medical device operatively coupled with a console. The medical device includes an elongate probe configured for insertion into a patient body, where the elongate probe includes a lumen extending along the elongate probe between a proximal end and a distal end. An optical fiber is disposed within the lumen, and an atraumatic tip is disposed at the distal end. The atraumatic tip defines two or more patient contact surfaces disposed along a distal tip section of the elongate probe, where a lateral separation distance between any two of the two or more patient contact surfaces is greater than a diameter of the elongate probe.

The console includes: a light source; an optical receiver; one or more processors and a non-transitory computer-readable medium having stored thereon logic that, when executed by the one or more processors, causes operations of the system. The operations include at least one of (i) projecting light away from the distal end of the elongate probe or (ii) determining a physical state of the elongate probe within the patient body.

In some embodiments, the distal tip section is formed into a loop. In other embodiments, the atraumatic tip includes a coil member having a number of coil windings wrapped around the distal tip section. In further embodiments, the distal tip section is formed into a curl, where the curl includes a number of curl windings wrapped around a winding axis oriented perpendicular to a longitudinal axis of the distal tip section. In still further embodiments, the distal tip section includes a radially expanded portion, where the radially expanded portion defines a diameter greater than a diameter of the elongate probe, and where in some embodiments, the radial expansion defines a bulbous shape.

In some embodiments, the atraumatic tip defines an attachment between the elongate probe and the optical fiber.

In some embodiments, the distal tip section defines a greater flexibility in bending than a main probe section, where the main probe section extends proximally away from the distal tip section.

In some embodiments, the distal tip section includes a varying flexibility in bending along a length of the distal tip section, where the varying flexibility includes a first flexibility in bending adjacent a proximal end of the distal tip section transitioning toward a second flexibility in bending adjacent a distal end of the distal tip section, and where the second flexibility in bending is greater than the first flexibility in bending.

In some embodiments, the elongate probe includes an actuator adjacent the proximal end, where the actuator is operatively coupled with the distal tip section. The actuator is configured to cause the distal tip section to laterally deflect between a first shape and a second shape based on manipulation of the actuator by a clinician, where the second shape is different from the first shape.

In some embodiments, the distal tip section includes a shape memory material having a shape transition temperature between about 20° C. and 37° C. In such embodiments, distal tip section defines a first transition shape below the transition temperature and a second transition shape above the transition temperature, where the second transition shape is different from the first transition shape.

In some embodiments, the optical fiber includes one or more core fibers extending along a longitudinal length of the optical fiber, where each of the one or more core fibers includes a plurality of sensors distributed along the longitudinal length, and where each sensor of the plurality of sensors is configured to (i) reflect a light signal of a different spectral width based on received incident light at proximal end, and (ii) change a characteristic of the reflected light signal based on condition experienced by the optical fiber. According to such embodiments, the operations include determining the physical state, where determining the physical state includes: (i) providing an incident light signal to the optical fiber; (ii) receiving reflected light signals of different spectral widths of the incident light by one or more of the plurality of sensors; and (iii) processing the reflected light signals associated with the one or more of core fibers to determine the physical state. In further accordance to such embodiments, the physical state includes one or more of a three-dimensional (3D) shape of the elongate probe, a temperature experienced by the elongate probe, a pressure exerted on the elongate probe, or a fluid flow adjacent the elongate probe.

In some embodiments, the optical fiber further includes: (i) one or more illuminating core fibers, where each of the one or more illuminating core fibers is configured to receive illuminating light from the console at the proximal end and project the illuminating light away from the distal end; and (ii) one or more imaging core fibers, where each of the one or more imaging core fibers is configured to receive imaging light at the distal end and propagate the imaging light along the optical fiber from the distal end to the console.

Further summarizing, also disclosed herein is a medical system that includes a medical device coupled with a console. The medical device includes an elongate probe configured for insertion into a patient body, where the elongate probe includes (i) a lumen extending along the elongate probe between a proximal end and a distal end and (ii) an optical fiber disposed within the lumen. An atraumatic tip disposed at the distal end includes a distal tip section that defines a greater flexibility in bending than a main probe section, where the main probe section extends proximally away from the distal tip section.

The console is operatively coupled with the medical device and includes: a light source; an optical receiver; one or more processors; and a non-transitory computer-readable medium having stored thereon logic that, when executed by the one or more processors, causes operations of the system. The operations include at least one of (i) projecting light away from the distal end of the elongate probe or (ii) determining a physical state of the elongate probe within the patient body.

In some embodiments, the distal tip section includes a varying flexibility in bending along a length of the distal tip section, where the varying flexibility includes a first flexibility in bending adjacent a proximal end of the distal tip section transitioning toward a second flexibility in bending adjacent a distal end of the distal tip section, and where the second flexibility in bending is greater than the first flexibility in bending.

In some embodiments, the elongate probe includes an actuator adjacent the proximal end operatively coupled with the distal tip section, where the actuator is configured to cause the distal tip section to laterally deflect between a first shape and a second shape based on manipulation of the actuator by a clinician, and where the second shape is different from the first shape.

In some embodiments, the distal tip section includes a shape memory material having a shape transition temperature between about 20° C. and 37° C. According to such embodiments, the distal tip section defines a first transition shape below the transition temperature and a second transition shape above the transition temperature, where the second transition shape is different from the first transition shape.

In some embodiments, the distal tip section or portion thereof is formed into a loop. In other embodiments, the atraumatic tip includes a coil member having a number of coil windings wrapped around the distal tip section. In further embodiments, the distal tip section or portion thereof is formed into a curl, where the curl includes a number of curl windings wrapped around a winding axis oriented perpendicular to a longitudinal axis of the distal tip section. In still further embodiments, the distal tip section includes a radially expanded portion, where the expanded portion defines a diameter greater than a diameter of the elongate probe.

In some embodiments, the atraumatic tip defines an attachment between the elongate probe and the optical fiber.

In some embodiments, the optical fiber includes one or more core fibers extending along a longitudinal length of the optical fiber, where each of the one or more core fibers includes a plurality of sensors distributed along the longitudinal length, and where each sensor of the plurality of sensors is configured to (i) reflect a light signal of a different spectral width based on received incident light at proximal end, and (ii) change a characteristic of the reflected light signal based on condition experienced by the optical fiber. According to such embodiments, the operations include determining the physical state, where determining the physical state includes: (i) providing an incident light signal to the optical fiber; (ii) receiving reflected light signals of different spectral widths of the incident light by one or more of the plurality of sensors; and (iii) processing the reflected light signals associated with the one or more of core fibers to determine the physical state. In further accordance to such embodiments, the physical state includes one or more of a three-dimensional (3D) shape of the elongate probe, a temperature experienced by the elongate probe, a pressure exerted on the elongate probe, or a fluid flow adjacent the elongate probe.

In some embodiments, the optical fiber further includes: (i) one or more illuminating core fibers, where each of the one or more illuminating core fibers is configured to receive illuminating light from the console at the proximal end and project the illuminating light away from the distal end; and (ii) one or more imaging core fibers, where each of the one or more imaging core fibers is configured to receive imaging light at the distal end and propagate the imaging light along the optical fiber from the distal end to the console.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 7 is a detailed illustration of a third embodiment the elongate probe of FIG. 1, in accordance with some embodiments; and FIG. 8 is a detailed illustration of a fourth embodiment the elongate probe of FIG. 1, in accordance with some embodiments.

DETAILED DESCRIPTION

Figure 1:
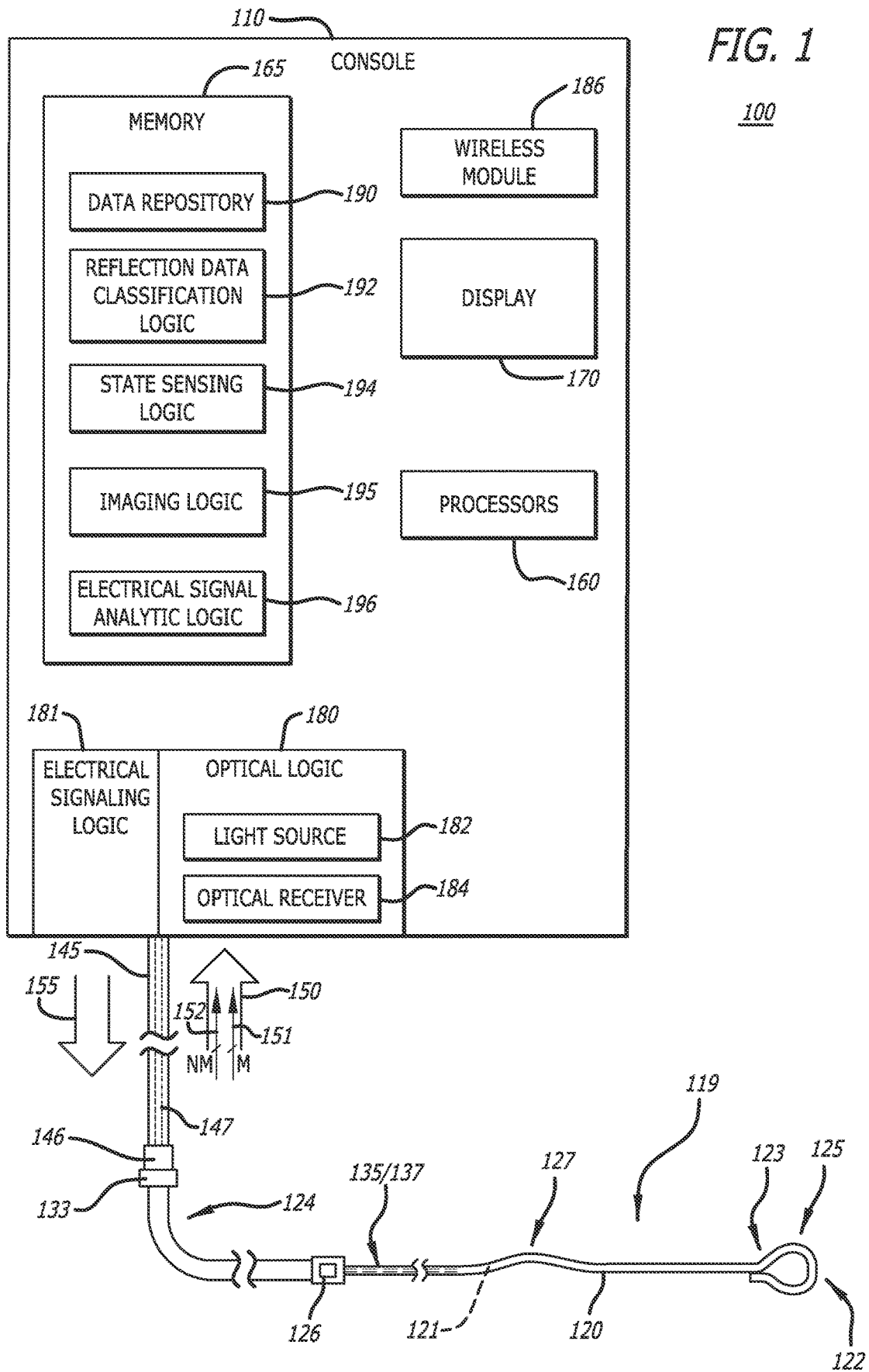
FIG. 1 is an illustrative embodiment of a medical device including a medical instrument with fiber optic sensing capabilities, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit (ASIC), etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

FIG. 1 illustrates an embodiment of a medical instrument placement system including a medical instrument. As shown, the medical instrument placement system (system) 100 generally includes a console 110 and an elongate probe 120 communicatively coupled with the console 110. The elongate probe 120 defines a distal end 122 and includes a console connector 133 at a proximal end 124. The elongate probe 120 includes an optical fiber 135 including multiple core fibers extending along a length of the elongate probe 120 as further described below. The console connector 133 enables the elongate probe 120 to be operably connected to the console 110 via an interconnect 145 including one or more optical fibers 147 (hereinafter, "optical fiber(s)") and an electrically conductive medium terminated by a single optical/electric connector 146 (or terminated by dual connectors). Herein, the connector 146 is configured to engage (mate) with the console connector 133 to allow for the propagation of light between the console 110 and the elongate probe 120 as well as the optional propagation of electrical signals from the elongate probe 120 to the console 110.

The elongate probe 120 may be configured to perform any of a variety of medical procedures. As such, the elongate probe 120 may be a component of or employed with a variety of medical instruments/devices 119. In some implementations, the elongate probe 120 may take the form of a guidewire or a stylet, for example. The elongate probe 120 may be formed of a metal, a plastic or a combination thereof. The elongate probe 120 includes a lumen 121 extending therealong having an optical fiber 135 disposed therein.

In some embodiments, the optical fiber 135 may be attached to the probe 120 at the distal end 122. More specifically, the optical fiber 135 may be attached to the probe 120 only at a single attachment at the distal end 122. As such, the optical fiber 135 may be unattached to the probe 120 except at the distal end 122. By attaching the optical fiber 135 to the probe 120 only at the distal end 122, the portion of optical fiber 135 extending proximally way from the distal end 122 is allowed to float (longitudinally slide) within the lumen 121. The floatability of the optical fiber 135 within the lumen 121 may prevent the probe 120 (or more specifically, the structure of the probe 120 such as a cylindrical wall of the probe 120, for example) from causing an undesirable strain along the optical fiber 135, where the undesirable strain may result in a decrease of shape sensing accuracy. In some embodiments, the optical fiber 135 may be attached to the probe 120 via an adhesive (not shown).

The elongate probe 120 includes a distal tip section 123 and main probe section 127 extending proximally away from the distal tip section 123. An atraumatic tip 125 is disposed at the distal end 122. The atraumatic tip 125 may include all or a portion of the distal tip section 123. The atraumatic tip 125 is generally configured to facilitate atraumatic insertion of the elongate probe 120 into a patient body (e.g., advancement along a vasculature of the patient body). The atraumatic tip 125 is configured to inhibit trauma to patient tissue during insertion. For example, the atraumatic tip 125 may be configured to prevent jabbing, poking, or snagging of a blood vessel wall during advancement. In some embodiments, portions of the elongate probe 120 may include sharp points or edges adjacent the distal end 122, and as such, the atraumatic tip 125 may be configured to prevent contact of the sharp points or edges with patient tissue. In some embodiments, the atraumatic tip 125 may include a number of patient contact surfaces configured to define a sliding contact with the patient tissue.

In some implementations, the elongate probe 120 may be integrated into a vascular catheter. Other exemplary implementations include drainage catheters, surgery devices, stent insertion and/or removal devices, biopsy devices, endoscopes, and kidney stone removal devices. In short, the elongate probe 120 may be employed with, or the elongate probe 120 may be a component of, any medical device 119 that is inserted into a patient.

According to one embodiment, the console 110 includes one or more processors 160, a memory 165, a display 170, and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The one or more processors 160, with access to the memory 165 (e.g., non-volatile memory or non-transitory, computer-readable medium), are included to control functionality of the console 110 during operation. As shown, the display 170 may be a liquid crystal diode (LCD) display integrated into the console 110 and employed as a user interface to display information to the clinician, especially during an instrument placement procedure. In another embodiment, the display 170 may be separate from the console 110. Although not shown, a user interface is configured to provide user control of the console 110.

According to the illustrated embodiment, the content depicted by the display 170 may change according to which mode the elongate probe 120 is configured to operate: optical, TLS, ECG, or another modality. In TLS mode, the content rendered by the display 170 may constitute a two-dimensional or three-dimensional representation of the physical state (e.g., length, shape, form, and/or orientation) of the elongate probe 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below.

According to one embodiment of the disclosure, an activation control 126, included on the elongate probe 120, may be used to set the elongate probe 120 into a desired operating mode and selectively alter operability of the display 170 by the clinician to assist in medical device placement. For example, based on the modality of the elongate probe 120, the display 170 of the console 110 can be employed for optical modality-based guidance during probe advancement through the vasculature or TLS modality to determine the physical state (e.g., length, form, shape, orientation, etc.) of the elongate probe 120. In one embodiment, information from multiple modes, such as optical, TLS or ECG for example, may be displayed concurrently (e.g., at least partially overlapping in time).

Referring still to FIG. 1, the optical logic 180 is configured to support operability of the elongate probe 120 and enable the return of information to the console 110, which may be used to determine the physical state associated with the elongate probe 120 along or an image of the patient body. Electrical signals, such as ECG signaling, may be processed via an electrical signaling logic 181 that supports receipt and processing of the received electrical signals from the elongate probe 120, (e.g., ports, analog-to-digital conversion logic, etc.). The physical state of the elongate probe 120 may be based on changes in characteristics of the reflected light signals 150 received at the console 110 from the elongate probe 120. The characteristics may include shifts in wavelength caused by strain on certain regions of the core fibers integrated within the optical fiber 135 positioned within or operating as the elongate probe 120, as shown below. As discussed herein, the optical fiber 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to an optical fiber 135. From information associated with the reflected light signals 150, the console 110 may determine (through computation or extrapolation of the wavelength shifts) the physical state of the elongate probe 120.

According to one embodiment of the disclosure, as shown in FIG. 1, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the optical fiber 135 within the elongate probe 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the optical fiber 135 deployed within the elongate probe 120, and (ii) translate the reflected light signals 150 into reflection data (from a data repository 190), namely data in the form of electrical signals representative of the reflected light signals including wavelength shifts caused by strain. The reflected light signals 150 associated with different spectral widths may include reflected light signals 151 provided from sensors positioned in the center core fiber (reference) of the optical fiber 135 and reflected light signals 152 provided from sensors positioned in the periphery core fibers of the optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the one or more processors 160, which governs their operation. Also, the optical receiver 184 is operably coupled to provide the reflection data (from the data repository 190) to the memory 165 for storage and processing by reflection data classification logic 192. The reflection data classification logic 192 may be configured to: (i) identify which core fibers pertain to which of the received reflection data (from the data repository 190) and (ii) segregate the reflection data stored within the data repository 190 provided from reflected light signals 150 pertaining to similar regions of the elongate probe 120 or spectral widths into analysis groups. The reflection data for each analysis group is made available to state sensing logic 194 for analytics.

According to one embodiment of the disclosure, the state sensing logic 194 is configured to compare wavelength shifts measured by sensors deployed in each periphery core fiber at the same measurement region of the elongate probe 120 (or same spectral width) to the wavelength shift at a center core fiber of the optical fiber 135 positioned along central axis and operating as a neutral axis of bending. From these analytics, the state sensing logic 194 may determine the shape the core fibers have taken in three-dimensional space and may further determine the current physical state of the elongate probe 120 in three-dimensional space for rendering on the display 170.

According to one embodiment of the disclosure, the state sensing logic 194 may generate a rendering of the current physical state of the elongate probe 120, based on heuristics or run-time analytics. For example, the state sensing logic 194 may be configured in accordance with machine-learning techniques to access the data repository 190 with pre-stored data (e.g., images, etc.) pertaining to different regions of the elongate probe 120 in which reflected light from core fibers have previously experienced similar or identical wavelength shifts. From the pre-stored data, the current physical state of the elongate probe 120 may be rendered. Alternatively, as another example, the state sensing logic 194 may be configured to determine, during run-time, changes in the physical state of each region of the optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the optical fiber 135 to the wavelength shift generated by a sensor of the center core fiber at the same cross-sectional region. It is contemplated that other processes and procedures may be performed to utilize the wavelength shifts as measured by sensors along each of the core fibers within the optical fiber 135 to render appropriate changes in the physical state of the elongate probe 120, especially to enable guidance of the elongate probe 120 when positioned multi-core within the patient and at a desired destination within the body.

The light source 182 and the optical receiver 184 may also be configured to provide illuminating light to the optical fiber 135 and receive imaging light signals from the optical fiber 135, respectively. The imaging logic 195 may be configured to (i) process imaging light signals, (ii) extract/determine an image from the imaging light signals, and (iii) cause the image to be portrayed on the display 170.

The console 110 may further include optional electrical signaling logic 181 configured to receive one or more electrical signals from the elongate probe 120. The elongate probe 120 is configured to support both optical connectivity as well as electrical connectivity. The electrical signaling logic 181 receives the electrical signals (e.g., ECG signals) from the elongate probe 120 via the conductive medium. The electrical signal logic 196 may process by to extract an ECG signal from the electrical signals. The electrical signal logic 196 may further cause an ECG waveform to be portrayed on the display 170.

It is contemplated that other processes and procedures may be performed to utilize the wavelength shifts as measured by sensors along each of the core fibers within the optical fiber 130 to render appropriate changes in the physical state of the probe 120, especially to enable guidance of the probe 120 when positioned multi-core within the patient and at a desired destination within the body. For example, wavelength shifts as measured by sensors along one or more of the core fibers may be based on physical states or condition of the probe 120 other than or in addition to longitudinal strain experienced by the elongate probe 120. Alternative or additional physical states may include one or more of torsional strain, temperature, motion, oscillations, pressure, or fluid flow adjacent the elongate probe.

Figure 2:
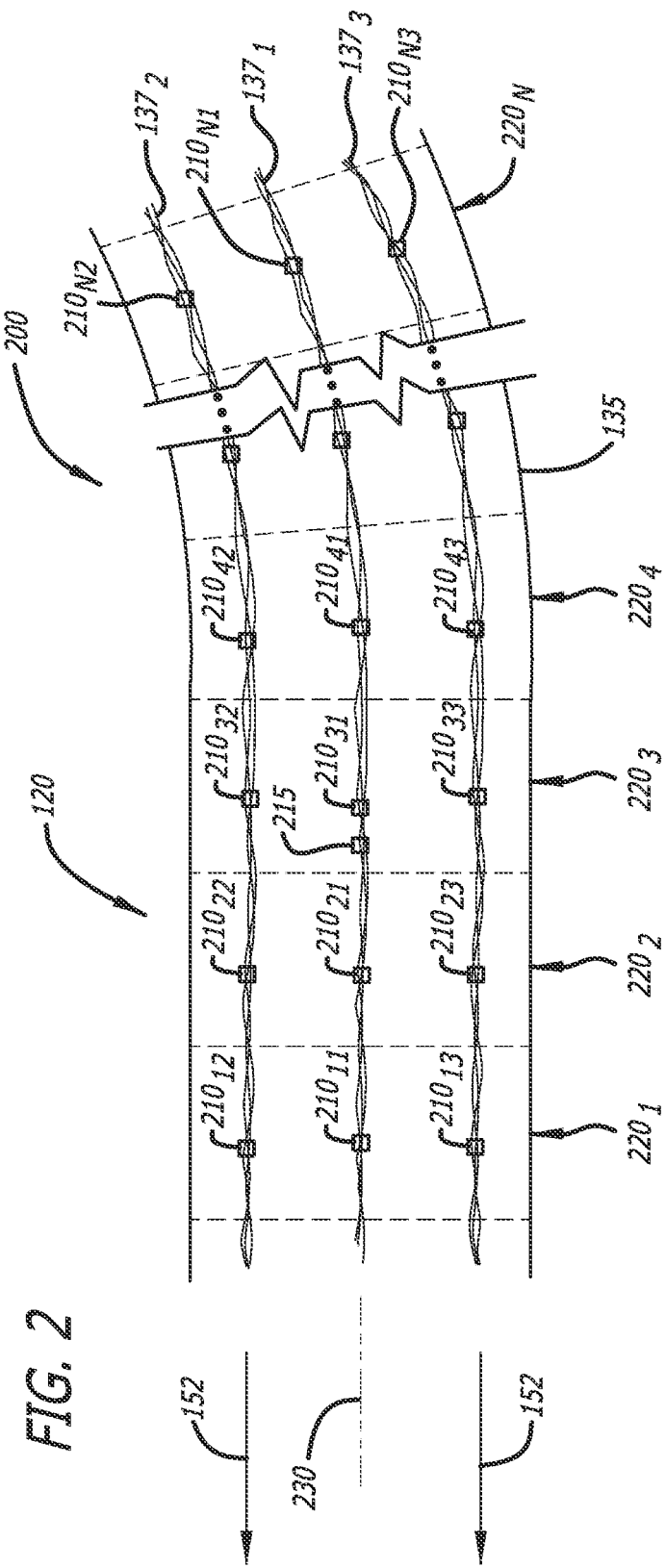
FIG. 2 is an exemplary embodiment of a structure of a section of the multi-core optical fiber included within the elongate probe of FIG. 1, in accordance with some embodiments.

Referring to FIG. 2, an exemplary embodiment of a structure of a section of the multi-core optical fiber included within the elongate probe 120 of FIG. 1 is shown in accordance with some embodiments. The multi-core optical fiber section 200 of the optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ ... $210_{N1}$-$210_{N4}$. Some or all of the cross-sectional regions $220_1$ ... $220_N$ may be static (e.g., prescribed length) or may be dynamic (e.g., vary in size among the regions $220_1$ ... $220_N$). A first core fiber $137_1$ is positioned substantially along a center (neutral) axis 230 while core fiber $137_2$ may be oriented within the cladding of the optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the elongate probe 120 is operative, each of the reflective gratings $210_1$-$210_N$ reflects light for a different spectral width. As shown, each of the gratings $210_{1i}$-$210_{Ni}$ ($1 \le i \le M$) is associated with a different, specific spectral width, which would be represented by different center frequencies of $f_1$ ... $f_n$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the elongate probe 120) based on wavelength shifts measured from the returned, reflected light. In particular, strain (e.g., compression or tension) applied to the optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the elongate probe 120 advances in the patient.

For example, with respect to the multi-core optical fiber section 200 of FIG. 2, in response to angular (e.g., radial) movement of the elongate probe 120 is in the left-veering direction, the fourth core fiber $137_4$ (see FIG. 3A) of the optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the elongate probe 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the optical fiber 135. These degrees of wavelength change may be used to extrapolate the physical state of the elongate probe 120. The reflected light signals 150 are reflected back to the console 110 via individual paths over a particular core fiber $137_1$-$137_M$.

In some embodiments, although not required, that the optical fiber 135 may include sensors 215, where wavelength shifts as measured by the sensors 215 along the optical fiber 135 may be based on physical states or conditions of the probe 120 that include one or more than a temperature experienced by the elongate probe 120, a pressure exerted on the elongate probe 120, or a fluid flow (e.g., blood flow) adjacent the elongate probe 120. The sensors 215 may located along any of the core fibers 137 or along additional core fibers (not shown). In accordance with the sensors 215, the state sensing logic 194 may be configured to determine one or more of the temperature, the pressure, or the fluid flow.

Figure 3A:
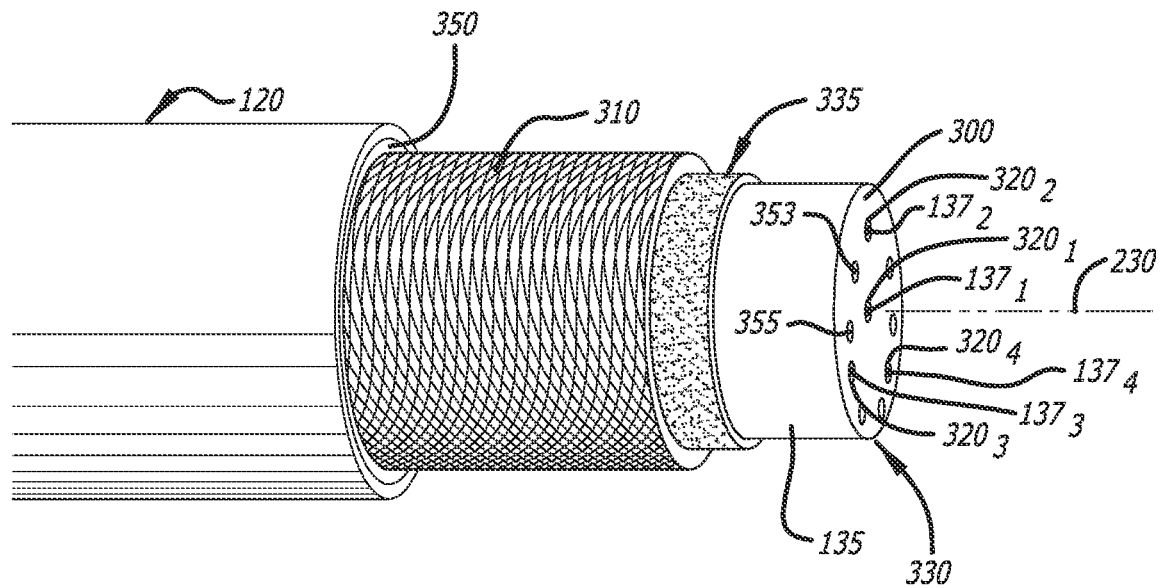
FIG. 3A illustrates an embodiment of the elongate probe of FIG. 1, in accordance with some embodiments.

Referring to FIG. 3A, a first exemplary embodiment of the elongate probe 120 of FIG. 1 supporting both an optical and electrical signaling is shown in accordance with some embodiments. Herein, the elongate probe 120 features a centrally located a multi-core optical fiber 135, which includes a cladding 300 and a plurality of core fibers $137_1$-$137_M$ (M≥2; M=4) residing within a corresponding plurality of lumens $320_1$-$320_M$. While the optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the optical fiber 135 and the elongate probe 120 deploying the optical fiber 135.

The optical fiber 135 is encapsulated within a concentric tubing 310 (e.g., braided tubing as shown) positioned over a low coefficient of friction layer 335. The concentric tubing 310, may in some embodiments, feature a "mesh" construction, in which the spacing between the intersecting elements may be selected based on the degree of rigidity/flexibility desired for the elongate probe 120, as a greater spacing may provide a lesser rigidity, and thereby, a more flexible elongate probe 120.

Figure 3B:
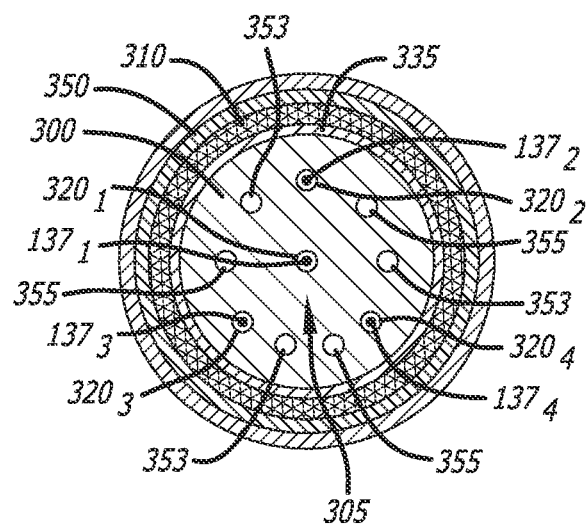
FIG. 3B is a cross sectional view of the elongate probe FIG. 3A, in accordance with some embodiments.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, the elongate probe 120 may optionally operate as an electrically conductive medium. In some embodiments, the concentric tubing 310 provides mechanical integrity to the optical fiber 135 and operates as a conductive pathway for electrical signals. For example, the concentric tubing 310 may be coupled with a distal tip section of the elongate probe 120. The cladding 300 and the concentric tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both the cladding 300 and the concentric tubing 310, as shown.

With further reference to FIG. 3B, the elongate probe 120 may optionally include a number of core fibers 353 configured for propagating illuminating light (e.g., the illuminating light 653 of FIG. 6) distally along the elongate probe 120 from the console connector 133 to the distal end 122. The illuminating light may project distally away from the distal end 122 (FIG. 1) of the elongate probe 120 to provide visual illumination to an interior portion of the patient body for the purpose of obtaining an image of the portion of the patient body, e.g., an image of an interior of a vascular lumen of the patient adjacent the distal end of the elongate probe 120.

The elongate probe 120 may further optionally include a number of core fibers 355 configured for propagating imaging light (e.g., the imaging light 655 of FIG. 6) proximally along the elongate probe 120 from the distal end 122 to the console connector 133. The imaging light, as may be defined by the illumination of the patient (e.g., an interior of a vascular lumen of the patient adjacent the distal end of the elongate probe 120), may be received by the core fibers 355 at the distal end 122.

Figure 4A:
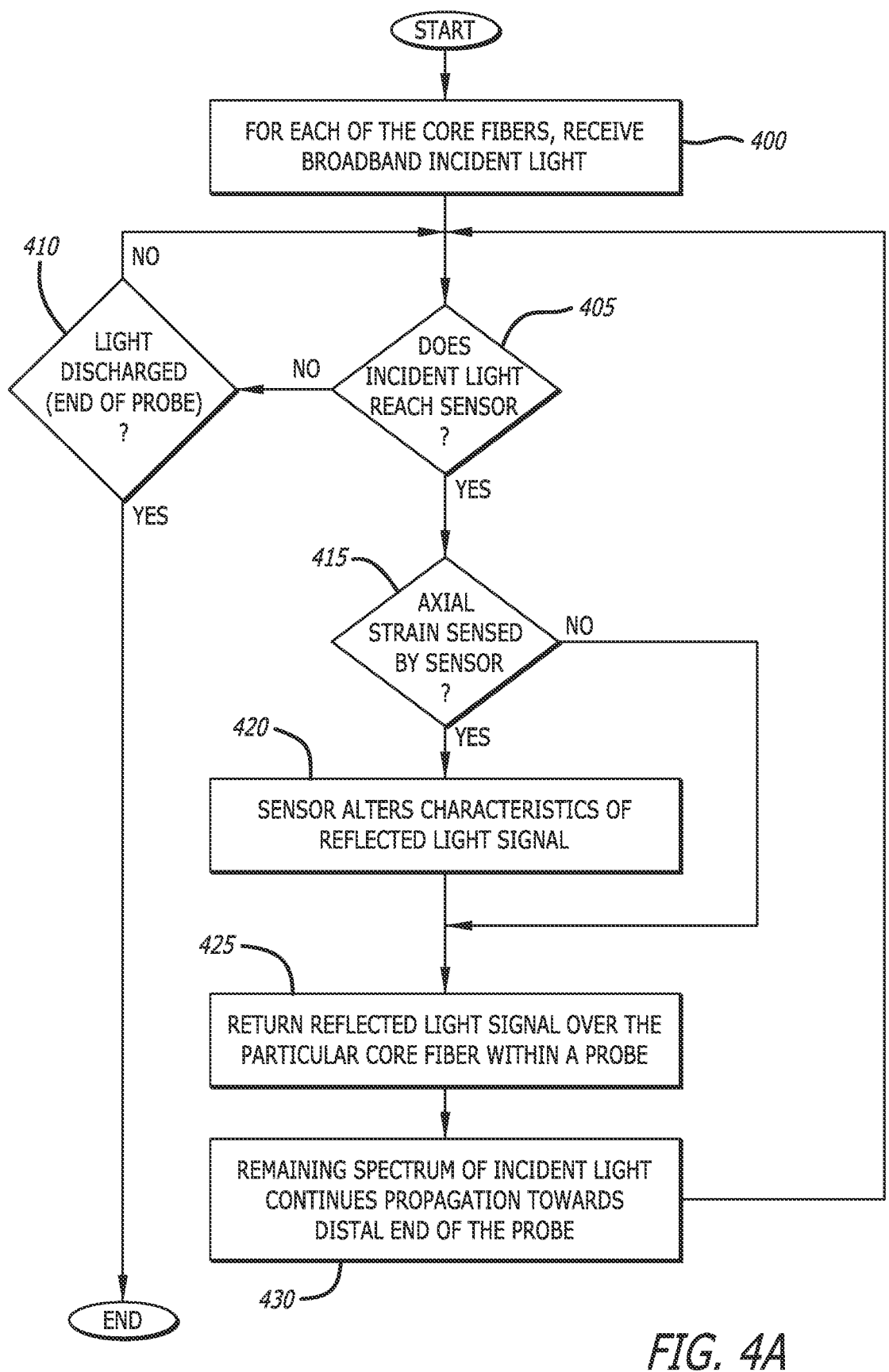
FIGS. 4A-4B are flowcharts of the methods of operations conducted by the medical device monitoring system of FIG. 1 to achieve optic three-dimensional shape sensing, in accordance with some embodiments.
Figure 4B:
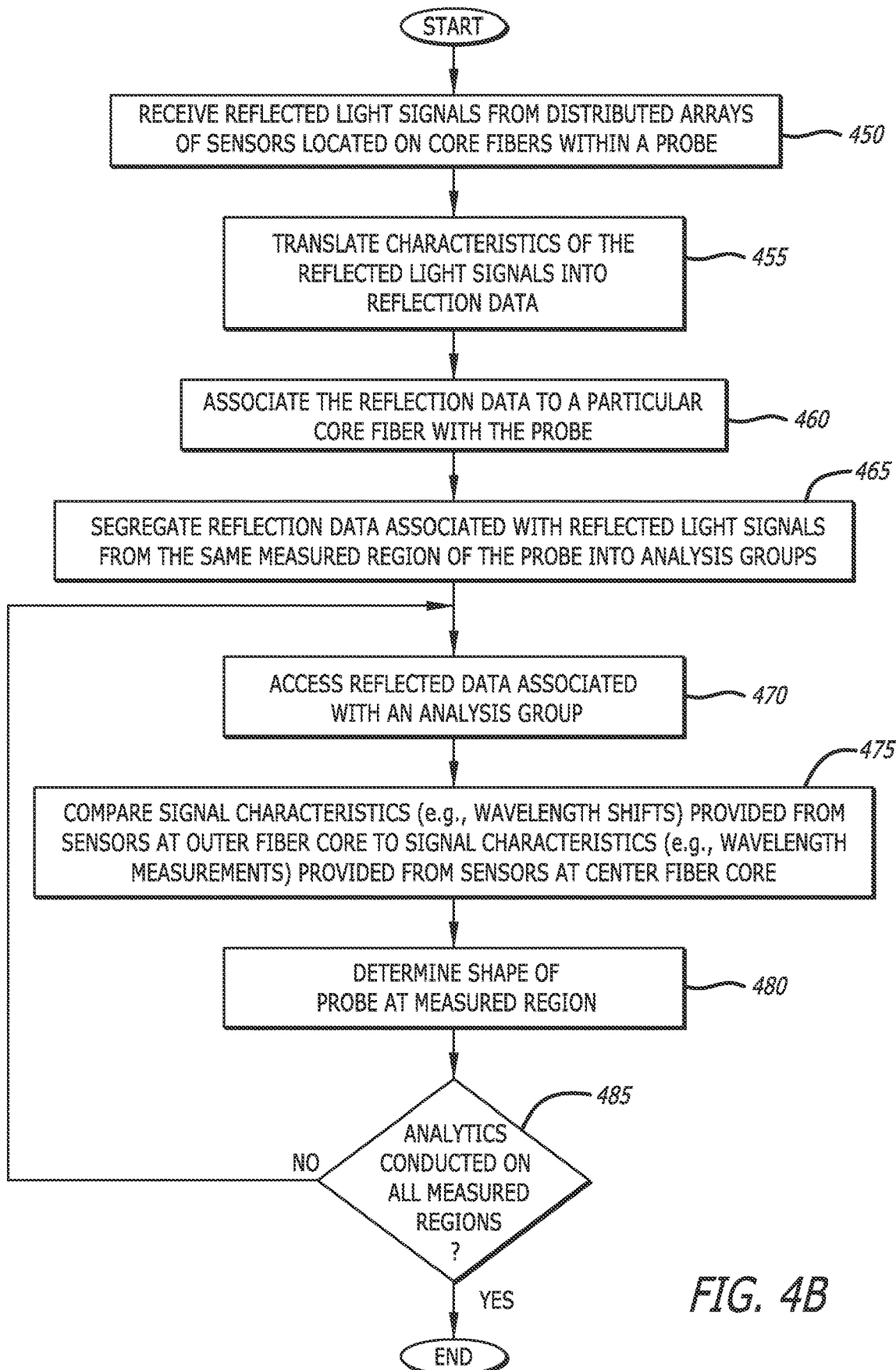

Referring to FIGS. 4A-4B, flowcharts of methods of operations conducted by the medical device system of FIG. 1 to achieve optic three-dimensional shape sensing are shown in accordance with some embodiments. The first micro-lumen is coaxial with the central axis of the probe. The first micro-lumen is configured to retain a center core fiber. Two or more micro-lumen, other than the first micro-lumen, are positioned at different locations circumferentially spaced along the circumferential edge of the probe. For example, two or more of the second plurality of micro-lumens may be positioned at different quadrants along the circumference edge of the probe.

Furthermore, each core fiber includes a plurality of sensors spatially distributed along its length between at least the proximal and distal ends of the probe. This array of sensors is distributed to position sensors at different regions of the core fiber to enable distributed measurements of strain throughout the entire length or a selected portion of the probe. These distributed measurements may be conveyed through reflected light of different spectral widths (e.g., specific wavelength or specific wavelength ranges) that undergoes certain wavelength shifts based on the type and degree of strain, including oscillations of the strain.

According to one embodiment of the disclosure, as shown in FIG. 4A, for each core fiber, broadband incident light is supplied to propagate through a particular core fiber (block 400). Unless discharged, upon the incident light reaching a sensor of a distributed array of sensors measuring strain on a particular core fiber, light of a prescribed spectral width associated with the first sensor is to be reflected back to an optical receiver within a console (blocks 405-410). Herein, the sensor alters characteristics of the reflected light signal to identify the type and degree of strain on the particular core fiber as measured by the first sensor (blocks 415-420). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the probe (blocks 425-430). The remaining spectrum of the incident light may encounter other sensors of the distributed array of sensors, where each of these sensors would operate as set forth in blocks 405-430 until the last sensor of the distributed array of sensors returns the reflected light signal associated with its assigned spectral width and the remaining spectrum is discharged as illumination.

Referring now to FIG. 4B, during operation, multiple reflected light signals are returned to the console from each of the plurality of core fibers residing within the corresponding plurality of micro-lumens formed within a probe. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 450-455). The reflection data classification logic is configured to identify which core fibers pertain to which reflection data and segregate reflection data provided from reflected light signals pertaining to a particular measurement region (or similar spectral width) into analysis groups (block 460-465).

Each analysis group of reflection data is provided to sensing logic for analytics (block 470). Herein, the sensing logic compares wavelength shifts at each outer core fiber with the wavelength shift at the center core fiber positioned along central axis and operating as a neutral axis of bending (block 475). From this analytics, on all analytic groups (e.g., reflected light signals from sensors in all or most of the core fibers), the sensing logic may determine the shape the core fibers have taken in three-dimensional space, from which the sensing logic can determine the current physical state of the probe in three-dimensional space (blocks 480-485).

Figure 5A:
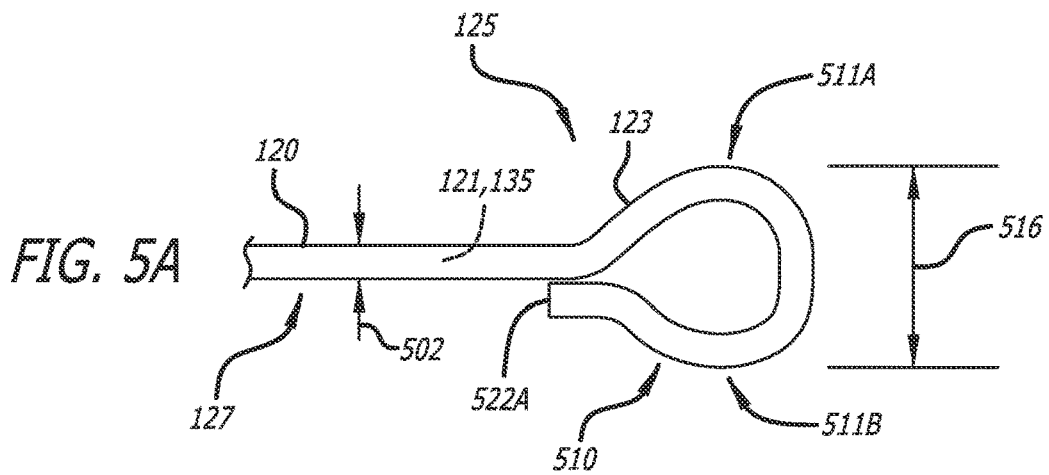
FIG. 5A is a detailed illustration of a distal portion of the elongate probe of FIG. 1 showing a first embodiment of the atraumatic tip, in accordance with some embodiments.

FIG. 5A is a detailed illustration of a distal portion of the elongate probe 120 including the distal tip section 123 and the atraumatic tip 125. According to a first embodiment, the atraumatic tip 125 includes a loop 510 formed of the distal tip section 123. In other words, the distal tip section 123 (or portion thereof) is curved to define the loop 510. Although not required, a distal most end 522A of the elongate probe 120 may attached to the elongate probe 120 to define a closed loop.

The loop 510 defines a first patient contact surface 511A disposed along a first lateral side of the loop 510 and a second patient contact surface 511B disposed along a second lateral side of the loop 510 opposite the first lateral side. The first patient contact surface 511A and the second patient contact surface 511B face away from each other. The first and second patient contact surfaces 511A, 511B are disposed along a smooth outside surface of the loop 510 so as to promote atraumatic contact with patient tissue during use within the patient body. The first and second patient contact surfaces 511A, 511B are spaced away from each other by a distance 516 that is greater than a diameter 502 of the elongate probe 120. As shown, the first and second patient contact surfaces 511A, 511B may inhibit contact of the distal most end 522A with the patient tissue.

As shown, the optical fiber 135 extends along the distal tip section 123. In some embodiments, the optical fiber 135 may extend distally to the distal most end 522A. In some embodiments, the atraumatic tip 125 may define an attachment between the elongate probe 120 and the optical fiber 135. In some embodiments, the loop 510 (or more specifically, the curved portion of the distal tip section 123 define the attachment, such as an interference fit of the optical fiber 135 within the lumen 121 along the curved portion of the distal tip section 123. In other embodiments, the attachment may be defined by an adhesive (note shown). In some embodiments, the attachment between the distal tip section 123 and the optical fiber 135 may be the only attachment. As such, the optical fiber 135 may be unattached to the elongate probe 120 along the main probe section 127.

Figure 5B:
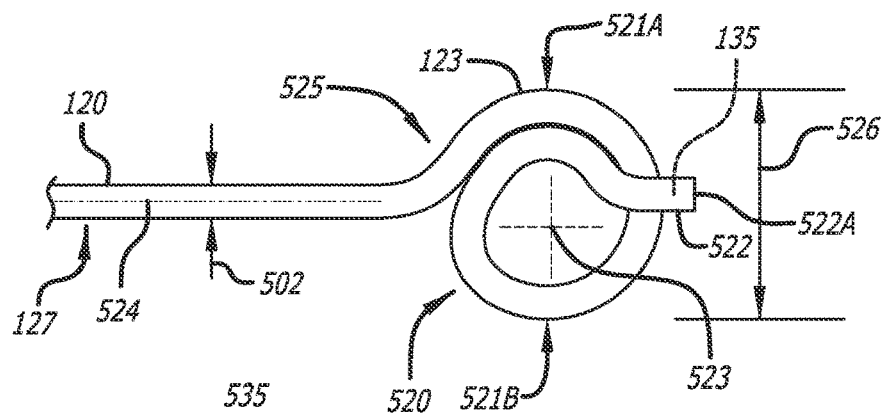
FIG. 5B is a detailed illustration of a distal portion of the elongate probe of FIG. 1 showing a second embodiment of the atraumatic tip, in accordance with some embodiments.

FIG. 5B illustrates a second embodiment of the atraumatic tip. The atraumatic tip 525 may resemble some components and functionality of the atraumatic tip 125. According to some embodiments, the atraumatic tip 525 includes a curl 520 formed of the distal tip section 123. In other words, the distal tip section 123 (or portion thereof) is coiled to define the curl 520. The curl 520 includes a number (e.g., 1, 2, 3, or more) of windings wrapped around a winding axis 522 (shown perpendicular to the page) that is substantially perpendicular to a longitudinal axis 524 of the elongate probe 120. In some embodiments, the curl 520 is configured to orient the distal most end 522A in a distal direction which may be parallel with the longitudinal axis 524.

The curl 520 defines a first patient contact surface 521A disposed along a first lateral side of the curl 520 and a second patient contact surface 521B disposed along a second lateral side of the curl 520 opposite the first side. As such, the first patient contact surface 521A and the second patient contact surface 521B face away from each other. The first and second patient contact surfaces 521A, 521B are disposed along a smooth outside surface of the curl 520 (or more specifically one or more windings of the curl 520) so as to promote atraumatic contact with patient tissue during use within the patient body. The first and second patient contact surfaces 521A, 521B are spaced away from each other by a distance 526 that is greater than the diameter 502 of the elongate probe 120. As shown, the first and second patient contact surfaces 511A, 511B may inhibit contact of the distal most end 522A with the patient tissue.

As shown, the optical fiber 135 extends along the distal tip section 123. In some embodiments, the optical fiber 135 may extend distally to the distal most end 522A so that as distal end of optical fiber 135 is oriented in the distal direction. Similar to the atraumatic tip 125, the atraumatic tip 525 may define an attachment between the elongate probe 120 and the optical fiber 135. In some embodiments, the curl 520 (or more specifically, the curved portion of the distal tip section 123 define the attachment, such as an interference fit of the optical fiber 135 within the lumen 121 along the curved portion of the distal tip section 123. In other embodiments, the attachment may be defined by an adhesive (note shown). In some embodiments, the attachment between the distal tip section 123 and the optical fiber 135 may be the only attachment. As such, the optical fiber 135 may be unattached to the elongate probe 120 along the main probe section 127.

Figure 5C:
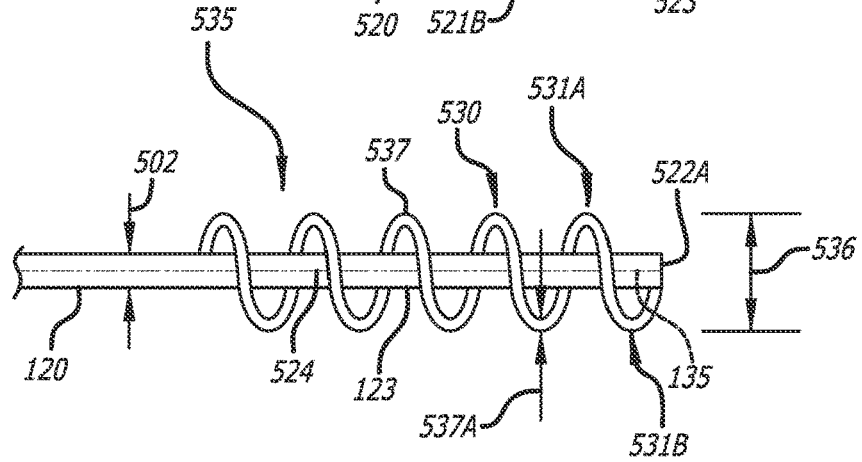
FIG. 5C is a detailed illustration of a distal portion of the elongate probe of FIG. 1 showing a third embodiment of the atraumatic tip, in accordance with some embodiments.

FIG. 5C illustrates a third embodiment of the atraumatic tip. The atraumatic tip 535 may resemble some components and functionality of the atraumatic tips 125, 525. According to some embodiments, the atraumatic tip 535 includes a coil 530 formed of a coil member 537 wrapped around the distal tip section 123. The coil 530 includes a number (e.g., 1, 2, 3, or more) of windings wrapped around a longitudinal axis 524. The coil 530 may extend along a portion or an entirety of the distal tip section 123. The coil 530 may extend to distally to the distal most end 522A. The coil member 537 may be formed of any suitable material such a metal or plastic. The coil member 537 may be coupled with the distal tip section 123 via a hoop stress, an adhesive or any other suitable fashion. In some embodiments, the coil member 537 may be formed of a rib protruding radially away from the distal tip section 123.

The coil 530 defines a first patient contact surface 531A disposed along a first lateral side of the coil 530 and a second patient contact surface 531B disposed along a second lateral side of the coil 530 opposite the first lateral side. As such, the first patient contact surface 531A and the second patient contact surface 531B face away from each other.

The coil member 537 may include any suitable cross-sectional shape, i.e., the coil member 537 may be round, oblong, or rectangular in cross section. In some embodiments, coil member 537 may define a width 537A that is less than the diameter 502. In other embodiments, width 537A may be greater than the diameter 502. In some embodiments, the windings of the coil 530 may be positioned adjacent one another to define a smooth outside surface of the coil 530 so as to promote atraumatic contact with patient tissue during use within the patient body. The first and second patient contact surfaces 531A, 531B are spaced away from each other by a distance 536 that is greater than the diameter 502 of the elongate probe 120. As shown, the first and second patient contact surfaces 531A, 531B may inhibit contact of the distal most end 522A with the patient tissue. As shown, the optical fiber 135 extends along the distal tip section 123. The optical fiber 135 is disposed within the lumen 121 along the coil 530 and may extend to the distal most end 522A. The optical fiber 135 may be attached to the elongate probe along the distal tip section 123.

Figure 5D:
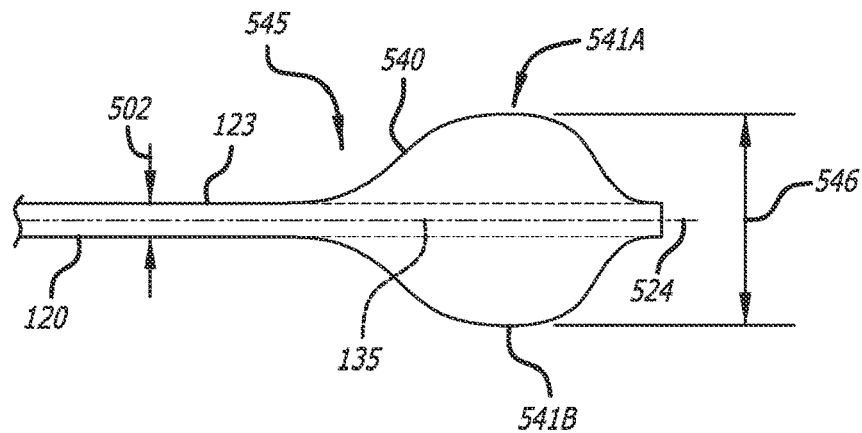
FIG. 5D is a detailed illustration of a distal portion of the elongate probe of FIG. 1 showing a fourth embodiment of the atraumatic tip, in accordance with some embodiments.

FIG. 5D illustrates a fourth embodiment of the atraumatic tip. The atraumatic tip 545 may resemble some components and functionality of the atraumatic tips 125, 525, and/or 535. According to some embodiments, the atraumatic tip 545 includes an expanded portion 540 of the distal tip section 123. The expanded portion 540 may be symmetrically defined about the longitudinal axis 524. In some embodiments, the expanded portion 540 may define a circular cross section about the longitudinal axis 524. In further embodiments, the expanded portion 540 may include a proximal tapered portion and/or a distal tapered portion. In other embodiments, the expanded portion 540 may be spherically shaped.

The 540 defines a first patient contact surface 541A disposed along a first lateral side of the expanded portion 540 and a second patient contact surface 541B disposed along a second lateral side of the expanded portion 540 opposite the first lateral side. As such, the first patient contact surface 541A and the second patient contact surface 541B face away from each other. The expanded portion 540 may be sized such that the first and second patient contact surfaces 541A, 541B are spaced away from each other by a distance 546 that is greater than the diameter 502 of the elongate probe 120. As shown, the first and second patient contact surfaces 541A, 541B may inhibit contact of the distal most end 522A with the patient tissue (e.g., a vascular wall). As shown, the optical fiber 135 extends along the distal tip section 123. The optical fiber 135 is within the lumen 121 along the expanded portion 540 and may extend to the distal most end 522A.

Figure 6:
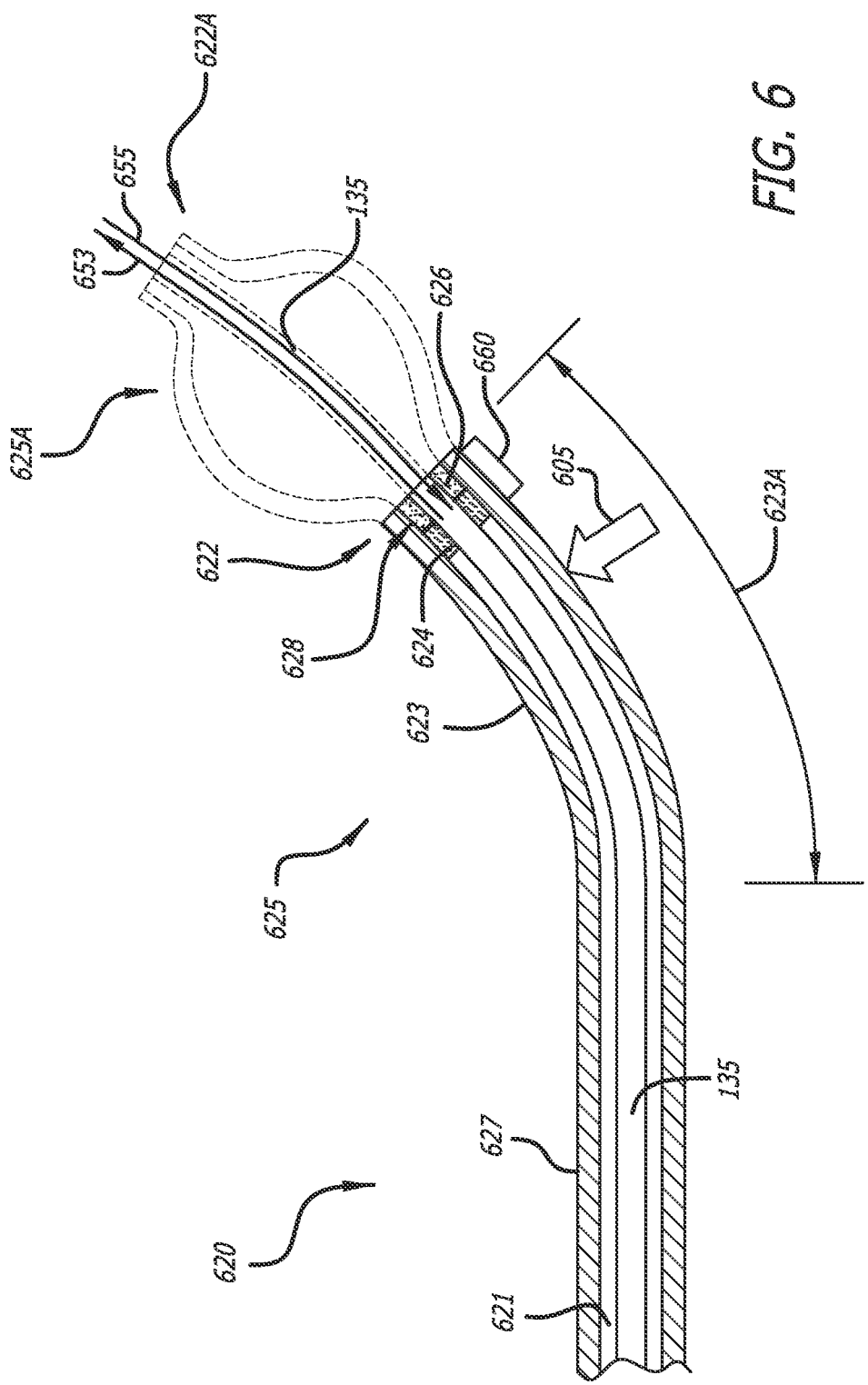
FIG. 6 is a detailed illustration of a second embodiment the elongate probe of FIG. 1, in accordance with some embodiments.

FIG. 6 illustrates another embodiment of an elongate probe that can, in certain respects, include and/or resemble components of the elongate probe 120 described in connection with FIGS. 1-5D. It will be appreciated that all the illustrated embodiments may have analogous features. Relevant disclosure set forth above regarding similar features thus may not be repeated hereafter. Moreover, specific features of the elongate probe and related components shown in FIGS. 1-5D may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the elongate probe of FIG. 6. Any suitable combination of the features, and variations of the same, described with respect to the elongate probe and components illustrated in FIGS. 1-5D can be employed with the elongate probe and components of FIG. 7, and vice versa. This pattern of disclosure applies equally to further embodiments depicted in subsequent figures and described hereafter.

FIG. 6 illustrates a detailed view of a distal portion of an elongate probe 620 having the optical fiber 135 disposed within the lumen 621 where the lumen 621 is defined by an annular wall 620. The elongate probe 620 includes a main probe section 627 disposed proximal of a distal tip section 623. The distal tip section 623 may define a length 623A between about 20 mm and 80 mm, between about 40 mm and 60 mm, or of about 50 mm. In FIG. 6, the distal tip section 623 is shown having a curved shape that may result from a lateral force 605 exerted onto the distal tip section 623 during use. In some embodiments, the distal tip section 623 may define a straight shape in a free state, i.e., in the absence of the lateral force 605.

The main probe section 623 is configured to enable a push-ability of the elongate probe 620 to facilitate insertion of the elongate probe 620 into the patient body, such as during advancement of the elongate probe 620 within a body lumen, for example. More specifically, the main probe section 621 may be sufficiently stiff to facilitate insertion of the elongate probe 620 into the patient body when pushed by a clinician from a location outside the patient body without the elongate probe 620 buckling within the patient body.

The distal tip section 623 may be more flexible in bending than the main probe section 627. In other words, the distal tip section 623 may be configured to deflect a greater amount than the main probe section 627 when the lateral force 605 is exerted thereon. The greater flexibility in bending of the distal tip section 623 may facilitate advancement along a body lumen (e.g., a blood vessel, a urethra, etc.) without causing tissue damage or trauma. More specifically, the distal tip section 623 may be configured to deflect due to contact with body tissue, such as a blood vessel wall, for example In some embodiments, the distal tip section 623 may include a varying flexibility in bending along the distal tip section 623. In other words, the distal tip section 623 may include a first flexibility in bending adjacent the main probe section 627 and a second flexibility in bending adjacent the distal end 622, where the second flexibility in bending is greater than the first flexibility in bending. In some embodiments, the first flexibility in bending may gradually transition toward the second flexibility in bending along the length 623A of the distal tip section 623.

The flexibility in bending of the distal tip section 623 may be defined by a structure of the annular wall 620 along the distal tip section 623, a material of the distal tip section 623, or both. Elements of a flexible structure may include one or more of slits, kerfs, bellows, coils, or the like. Flexible materials may include metals (e.g., Nitinol), polymeric materials or elastomeric materials, or any combination thereof.

In some embodiments, the distal tip section 623 may include an electrode 660 operatively coupled with (e.g., electrical connected to) the concentric tubing 310 to provide for the transmission of electrical signals from the electrode 660 to the console 110 (see FIG. 1). The electrode 660 may extend along an outside surface of elongate probe 620. For example, the electrode 660 may partially or entirely surround the elongate probe 620. In some embodiments, the electrode 660 may be electrically coupled with the distal tip section 623. As such, the distal tip section 623 may define a portion of the electrical connection between the electrode 660 and the concentric tubing 310.

In some embodiments, the probe 620 may include a sealing member 624 which, in some embodiments, may be disposed within the lumen 621 between probe 620 and the optical fiber 135 as illustrated. The sealing member 624 may be configured so that fluid exchange is prevented between the lumen 621 and the patient body. For example, the sealing member 624 may prevent body fluids from entering the lumen 621 and/or migrating proximally along the lumen 621. In some instances, a pressure within the patient adjacent the distal end 622 may be negative (i.e., vacuum). As such, the sealing member 624 may prevent air from migrating distally along the lumen 621 and entering the patient body. The sealing member 624 may take any form suitable for providing the seal. In some embodiments, the sealing member 624 may be an O-ring are similar device. In other embodiments, the sealing member 624 may be formed of a curable substance, such as a curable silicone sealant, for example. The sealing member 624 may be located at any position along the elongate member 620 suitable for sealing off the lumen 621. In some embodiments, the sealing member 624 may form a film covering the distal tip section 623 or a portion thereof.

The optical fiber 135 may be attached to the probe 620 at the distal end 622. More specifically, the optical fiber 135 may be attached to the probe 620 only at a single attachment point 628 located adjacent the distal end 622. As such, the optical fiber 135 is unattached to the probe 620 except at the distal end 622. By attaching the optical fiber 135 to the probe 620 only at the distal end 622, the portion of optical fiber 135 extending proximally way from the distal end 622 is allowed to float (longitudinally slide) within the lumen 621. The floatability of the optical fiber 135 within the lumen 621 may prevent the probe 620 from causing undesirable strain along the optical fiber 135, where the undesirable strain may result in a decrease of shape sensing accuracy. In some embodiments, the optical fiber 135 may be attached to the probe 620 via an adhesive 626.

In some embodiments, the distal tip section 623 may define the atraumatic tip 625. More specifically, the flexibility in bending of the distal tip section 623 may define the atraumatic tip 625. As illustrated in phantom lines, the atraumatic tip 625 may optionally include additional atraumatic features 625A, where the additional atraumatic features 625A include any one of the loop 510, the curl 520, the coil 530, or the expanded portion 540. In some embodiments, the optical fiber 135 may extend distally to a distal end 622A of the additional atraumatic features 625A.

The probe 620 may be configured to project an illuminating light 653 distally away from the distal end 622 of the elongate probe 620 to provide visual illumination to an interior portion of the patient for the purpose of obtaining an image of the patient body, e.g., an image of an interior of a vascular lumen of the patient adjacent the distal end of the elongate probe 620. The probe 620 may also be configured to receive an imaging light 655. The imaging light 655 may be defined by the illumination of the patient by the illuminating light 653.

FIG. 7 illustrates another embodiment of an elongate probe that can, in certain respects, include and/or resemble components of the elongate probe 620. The elongate probe 720 includes a steering capability to facilitate insertion within the patient body (e.g., advancement along a lumen of the patient body). Similar to the elongate probe 620, the elongate probe 720 includes a distal tip section 723 that is more flexible that the main probe section 727. The elongate probe 720 also includes a handle 750 having an actuator 751. The actuator 751 is operatively coupled with the distal tip section 723 at the distal end 722A via one or more connecting members 752 (e.g., wires or cables) extending along the elongate probe 720 between the handle 750 and the distal end 722. The connecting members 752 are coupled between the actuator 751 the distal end 722A such that manipulation of the actuator 751 by a clinician causes fore and/or aft longitudinal displacement of the connecting members 752 which in turn causes a unilateral or bilateral deflection of the distal tip section 723. More specifically, manipulation of the actuator 751 by the clinician may cause the distal tip section 723 to laterally deflect between a first shape and a second shape.

In use, the clinician may deflect the distal tip section 723 based on an image acquired by the elongate probe 720. For example, the clinician may advance the elongate probe 720 along a vasculature of the patient body and identify an optional vasculature pathway within an image acquired by the elongate probe 720. As a result of the identification, the clinician may deflect the distal tip section 723 toward or away from the optional vasculature pathway.

Similar to the probe 620, the distal tip section 723 may define the atraumatic tip 725. More specifically, the steering capability of the distal tip section 723 may define the atraumatic tip 725. As illustrated in phantom lines, the atraumatic tip 725 may optionally include additional atraumatic features 725A, where the additional atraumatic features 725A include any one of the loop 510, the curl 520, the coil 530, or the expanded portion 540. In some embodiments, the optical fiber 135 may extend distally to a distal end 722B of the additional atraumatic features 725A.

FIG. 8 illustrates another embodiment of an elongate probe. The elongate probe 820 generally defines a main probe section 827 and distal tip section 823. The distal tip section 823 is configured to define a first shape 823A and a second shape 823B. The first and second shapes 823A, 823B may exist in a free state, i.e., absent any external applied force to the distal tip section 823. The distal tip section 823 may be formed of a shape memory material 824 (e.g., Nitinol) to facilitate defining the first shape 823A and the second shape 823B.

The distal tip section 823 may be configured to define the first shape 823A at a first point in time and the second shape at a subsequent point in time. In some embodiments, the distal tip section 823 may (i) define the first shape 823A prior to insertion of the probe 820 within the patient body, and (ii) define the second shape 823B after the probe 820 is inserted within the patient body. In some embodiments, the first shape 823A may be substantially straight to facilitate insertion of the probe 820 into the patient, such as along a vascular access pathway, for example. Similarly, in some embodiments, the second shape 823B may be curved to enable steering of the probe 820 along a vasculature of the patient body.

In some embodiments, the distal tip section 823 may transition from the first shape 823A to the second shape 823B upon or during insertion of the probe 820 into the patient body. As the body temperature may be different than the environmental temperature, the distal tip section may be configured to (i) maintain the first shape 823A while the probe 820 is exposed to the environmental temperature, and (ii) transition from the first shape 823A to the second shape 823B when the probe 820 is exposed to the body temperature. As a typical room temperature is about 20° C. and a typical body temperature is about 37° C., the distal tip section 823 may define a transition temperature between 20° C. and 37° C. To account for a range of environmental temperatures, the distal tip section 822 may define a transition temperature that approaches 37° C. As such, the transition temperature of the distal tip section 822 may be between about 20° C. and 37° ° C., 30° C. and 37° ° C., or 33° C. and 36° C.

Similar to the probe 620, the distal tip section 823 may define the atraumatic tip 825. More specifically, the flexibility in bending and/or the transitioning from the first shape 823A to the second shape 823B of the distal tip section 823 may define the atraumatic tip 825. As illustrated in phantom lines, the atraumatic tip 825 may optionally include additional atraumatic features 825A, where the additional atraumatic features 825A include any one of the loop 510, the curl 520, the coil 530, or the expanded portion 540. In some embodiments, the optical fiber 135 may extend distally to a distal end 822B of the additional atraumatic features 825A.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical system comprising:
   a medical device comprising:
   an elongate probe configured for insertion into a patient body, the elongate probe including a lumen extending along the elongate probe between a proximal end and a distal end;
   an optical fiber disposed within the lumen, wherein the optical fiber is encapsulated in concentric tubing that includes a mesh construction, in which a spacing between intersecting elements of the mesh construction is selected based on a degree of rigidity/flexibility desired for the medical device; and
   an atraumatic tip at the distal end, wherein:
   the atraumatic tip defines two or more patient contact surfaces disposed along a distal tip section of the elongate probe, a lateral separation distance between any two of the two or more patient contact surfaces is greater than a diameter of the elongate probe, and the distal tip section is formed into a loop to define the atraumatic tip such that a distal end of the distal tip section is disposed adjacent the elongate probe proximal the loop; and a console operatively coupled with the medical device at the proximal end, the console including a light source, an optical receiver, one or more processors, and a non-transitory computer-readable medium having stored thereon logic that, when executed by the one or more processors, causes operations that include at least one of projecting light away from the distal end of the elongate probe or determining a physical state of the elongate probe within the patient body.

2. The system of claim 1, wherein the loop includes a number of windings wrapped around a winding axis oriented perpendicular to a longitudinal axis of the elongate probe to define a curl.

3. The system of claim 1, wherein the atraumatic tip defines an attachment between the elongate probe and the optical fiber.

4. The system of claim 1, wherein the distal tip section defines a greater flexibility in bending than a main probe section, the main probe section extending proximally away from the distal tip section.

5. The system of claim 4, wherein:
the distal tip section includes a varying flexibility in bending along a length of the distal tip section,
the varying flexibility includes a first flexibility in bending adjacent a proximal end of the distal tip section transitioning toward a second flexibility in bending adjacent the distal end of the distal tip section, and
the second flexibility in bending is greater than the first flexibility in bending.

6. The system of claim 1, wherein:
the elongate probe includes an actuator adjacent the proximal end;
the actuator is operatively coupled with the distal tip section; and
the actuator is configured to cause the distal tip section to laterally deflect between a first shape and a second shape based on manipulation of the actuator by a clinician, the second shape different from the first shape.

7. The system of claim 1, wherein:
the distal tip section includes a shape memory material having a shape transition temperature between about 20° C. and 37° C.,
the distal tip section defines a first transition shape below the shape transition temperature and a second transition shape above the shape transition temperature, and the second transition shape is different from the first transition shape.

8. The system of claim 1, wherein:
the optical fiber includes one or more core fibers extending along a longitudinal length of the optical fiber, each of the one or more core fibers including a plurality of sensors distributed along the longitudinal length and each sensor of the plurality of sensors being configured to (i) reflect a light signal of a different spectral width, the reflected light signal based on received incident light at the proximal end, and (ii) change a characteristic of the reflected light signal based on a condition experienced by the optical fiber;
the operations include determining the physical state;
determining the physical state includes:
providing an incident light signal to the optical fiber;
receiving reflected light signals of different spectral widths of the received incident light by one or more of the plurality of sensors; and
processing the reflected light signals associated with the one or more core fibers to determine the physical state; and
the physical state includes one or more of a three-dimensional (3D) shape of the elongate probe, a temperature experienced by the elongate probe, a pressure exerted on the elongate probe, or a fluid flow adjacent the elongate probe.

9. The system of claim 1, wherein the optical fiber further includes:
one or more illuminating core fibers, each of the one or more illuminating core fibers configured to receive illuminating light from the console at the proximal end and project the illuminating light away from the distal end; and
one or more imaging core fibers, each of the one or more imaging core fibers configured to receive imaging light at the distal end and propagate the imaging light along the optical fiber from the distal end to the console.

10. A medical system comprising:
a medical device comprising:
an elongate probe configured for insertion into a patient body, the elongate probe including a lumen extending along the elongate probe between a proximal end and a distal end;
an optical fiber disposed within the lumen, wherein the optical fiber is encapsulated in concentric tubing that includes a mesh construction, in which a spacing between intersecting elements of the mesh construction is selected based on a degree of rigidity/flexibility desired for the medical device; and
an atraumatic tip at the distal end, the atraumatic tip including a distal tip section that has a greater flexibility in bending than a main probe section, the main probe section extending proximally away from the distal tip section, wherein the distal tip section is formed into a loop to define the atraumatic tip such that a distal end of the distal tip section is disposed adjacent the elongate probe proximal the loop; and
a console operatively coupled with the medical device at the proximal end, the console including a light source, an optical receiver, one or more processors, and a non-transitory computer-readable medium having stored thereon logic that, when executed by the one or more processors, causes operations that include at least one of projecting light away from the distal end of the elongate probe or determining a physical state of the elongate probe within the patient body.

11. The system of claim 10, wherein:
the distal tip section includes a varying flexibility in bending along a length of the distal tip section,
the varying flexibility includes a first flexibility in bending adjacent a proximal end of the distal tip section transitioning toward a second flexibility in bending adjacent the distal end of the distal tip section, and
the second flexibility in bending is greater than the first flexibility in bending.

12. The system of claim 10, wherein:
the elongate probe includes an actuator adjacent the proximal end;
the actuator is operatively coupled with the distal tip section; and the actuator is configured to cause the distal tip section to laterally deflect between a first shape and a second shape based on manipulation of the actuator by a clinician, the second shape different from the first shape.

13. The system of claim 10, wherein:
the distal tip section includes a shape memory material having a shape transition temperature between about 20° C. and 37° C.,
the distal tip section defines a first transition shape below the shape transition temperature and a second transition shape above the shape transition temperature, and
the second transition shape is different from the first transition shape.

14. The system of claim 10, wherein the loop includes a number of windings wrapped around a winding axis oriented perpendicular to a longitudinal axis of the elongate probe to define a curl.

15. The system of claim 10, wherein the atraumatic tip defines an attachment between the elongate probe and the optical fiber.

16. The system of claim 10, wherein:
the optical fiber includes one or more core fibers extending along a longitudinal length of the optical fiber, each of the one or more core fibers including a plurality of sensors distributed along the longitudinal length and each sensor of the plurality of sensors being configured to (i) reflect a light signal of a different spectral width, the reflected light signal based on received incident light at the proximal end, and (ii) change a characteristic of the reflected light signal based on a condition experienced by the optical fiber;
the operations include determining the physical state;
determining the physical state includes:
providing an incident light signal to the optical fiber;
receiving reflected light signals of different spectral widths of the received incident light by one or more of the plurality of sensors; and
processing the reflected light signals associated with the one or more core fibers to determine the physical state; and
the physical state includes one or more of a three-dimensional (3D) shape of the elongate probe, a temperature experienced by the elongate probe, a pressure exerted on the elongate probe, or a fluid flow adjacent the elongate probe.

17. The system of claim 10, wherein the optical fiber further includes:
one or more illuminating core fibers, each of the one or more illuminating core fibers configured to receive illuminating light from the console at the proximal end and project the illuminating light away from the distal end; and
one or more imaging core fibers, each of the one or more imaging core fibers configured to receive imaging light at the distal end and propagate the imaging light along the optical fiber from the distal end to the console.

* * * * *